US012690838B2

(12) United States Patent
Takenouchi

(10) Patent No.: US 12,690,838 B2
(45) Date of Patent: Jul. 28, 2026

(54) IMAGE PROCESSING APPARATUS, IMAGE PROCESSING SYSTEM, IMAGE PROCESSING METHOD, AND IMAGE PROCESSING PROGRAM

(71) Applicant: FUJIFILM Corporation, Tokyo (JP)

(72) Inventor: Seiya Takenouchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 93 days.

(21) Appl. No.: 18/489,843

(22) Filed: Oct. 18, 2023

(65) Prior Publication Data

US 2024/0046600 A1 Feb. 8, 2024

Related U.S. Application Data

(63) Continuation of application No. PCT/JP2022/014345, filed on Mar. 25, 2022.

(30) Foreign Application Priority Data

May 10, 2021 (JP) ................................. 2021-079511

(51) Int. Cl.
*G06V 10/25* (2022.01)
*A61B 8/00* (2006.01)
(Continued)

(52) U.S. Cl.
CPC ................ *G06V 10/25* (2022.01); *A61B 8/12* (2013.01); *A61B 8/463* (2013.01); *A61B 8/469* (2013.01);
(Continued)

(58) Field of Classification Search
CPC .... G06V 10/25; G06V 2201/03; G06V 10/82; A61B 8/12; A61B 8/463; A61B 8/469;
(Continued)

(56) References Cited

U.S. PATENT DOCUMENTS 7,092,749 B2 * 8/2006 Fowkes .................. G16H 40/60
600/407
9,788,729 B2 10/2017 Waku et al.
(Continued)

FOREIGN PATENT DOCUMENTS

CN 101732061 6/2010
CN 112115938 A * 12/2020 ........... G06T 7/0012
(Continued)

OTHER PUBLICATIONS

"International Search Report (Form PCT/ISA/210) of PCT/JP2022/014345", mailed on May 24, 2022, with English translation thereof, pp. 1-5.
(Continued)

*Primary Examiner* — Xiao M Wu
(74) *Attorney, Agent, or Firm* — JCIPRNET

(57) ABSTRACT

An image processing apparatus according to an aspect of the present invention is an image processing apparatus including a processor. The processor is configured to execute an image acquisition process for acquiring an image, a recognition process for recognizing a region of interest from the image, a notification information determination process for determining first notification information indicating a position of the region of interest in the image and second notification information indicating a type of the region of interest, and a notification position determination process for determining a notification position at which a notification of the second notification information is to be presented in the image, on the basis of pixel values in an area surrounding the region of interest in the image.

19 Claims, 8 Drawing Sheets

(51) Int. Cl.

| | | |
|---|---|---|
| *A61B 8/12* | (2006.01) | |
| *G06T 7/00* | (2017.01) | |
| *G06T 7/66* | (2017.01) | |
| *G06T 7/70* | (2017.01) | |
| *G06T 11/60* | (2026.01) | |

(52) U.S. Cl.

CPC .............. *G06T 7/0016* (2013.01); *G06T 7/66* (2017.01); *G06T 7/70* (2017.01); *G06T 11/60* (2013.01); *G06T 2207/10068* (2013.01); *G06T 2207/10132* (2013.01); *G06V 2201/03* (2022.01)

(58) Field of Classification Search

CPC ..... A61B 8/5215; A61B 1/045; A61B 8/5207; G06T 7/0016; G06T 7/66; G06T 7/70; G06T 11/60; G06T 2207/10068; G06T 2207/10132; G16H 30/40

See application file for complete search history.

(56) References Cited

U.S. PATENT DOCUMENTS

| | | | |
|---|---|---|---|
| 10,799,098 | B2 | 10/2020 | Oosake |
| 2004/0254439 | A1 | 12/2004 | Fowkes et al. |

| | | | |
|---|---|---|---|
| 2012/0063661 | A1 | 3/2012 | Nishimura |
| 2020/0294227 | A1 | 9/2020 | Usuda |
| 2021/0366110 | A1 | 11/2021 | Oosake et al. |
| 2023/0181001 | A1 | 6/2023 | Usuda |

FOREIGN PATENT DOCUMENTS

| | | |
|---|---|---|
| JP | 2020044044 | 3/2020 |
| JP | 2020146202 | 9/2020 |
| WO | 2011013346 | 2/2011 |
| WO | 2018221033 | 12/2018 |
| WO | 2020183770 | 9/2020 |
| WO | 2021039101 | 3/2021 |

OTHER PUBLICATIONS

"Written Opinion of the International Searching Authority (Form PCT/ISA/237) of PCT/JP2022/014345", mailed on May 24, 2022, with English translation thereof, pp. 1-6.

"Search Report of Europe Counterpart Application", issued on Oct. 10, 2024, p. 1-p. 10.

"Office Action of China Counterpart Application", issued on Apr. 11, 2026, with English translation thereof, p. 1-p. 27.

\* cited by examiner

2

10

24

42
38
36

22

44

62
64
50
52
20a
54
20

30
32

28

14 — ENDOSCOPE PROCESSOR DEVICE

LIGHT SOURCE DEVICE — 16

WATER SUPPLY TANK — 70

34

26

ULTRASONIC PROCESSOR DEVICE

MONITOR — 18

SUCTION PUMP — 72

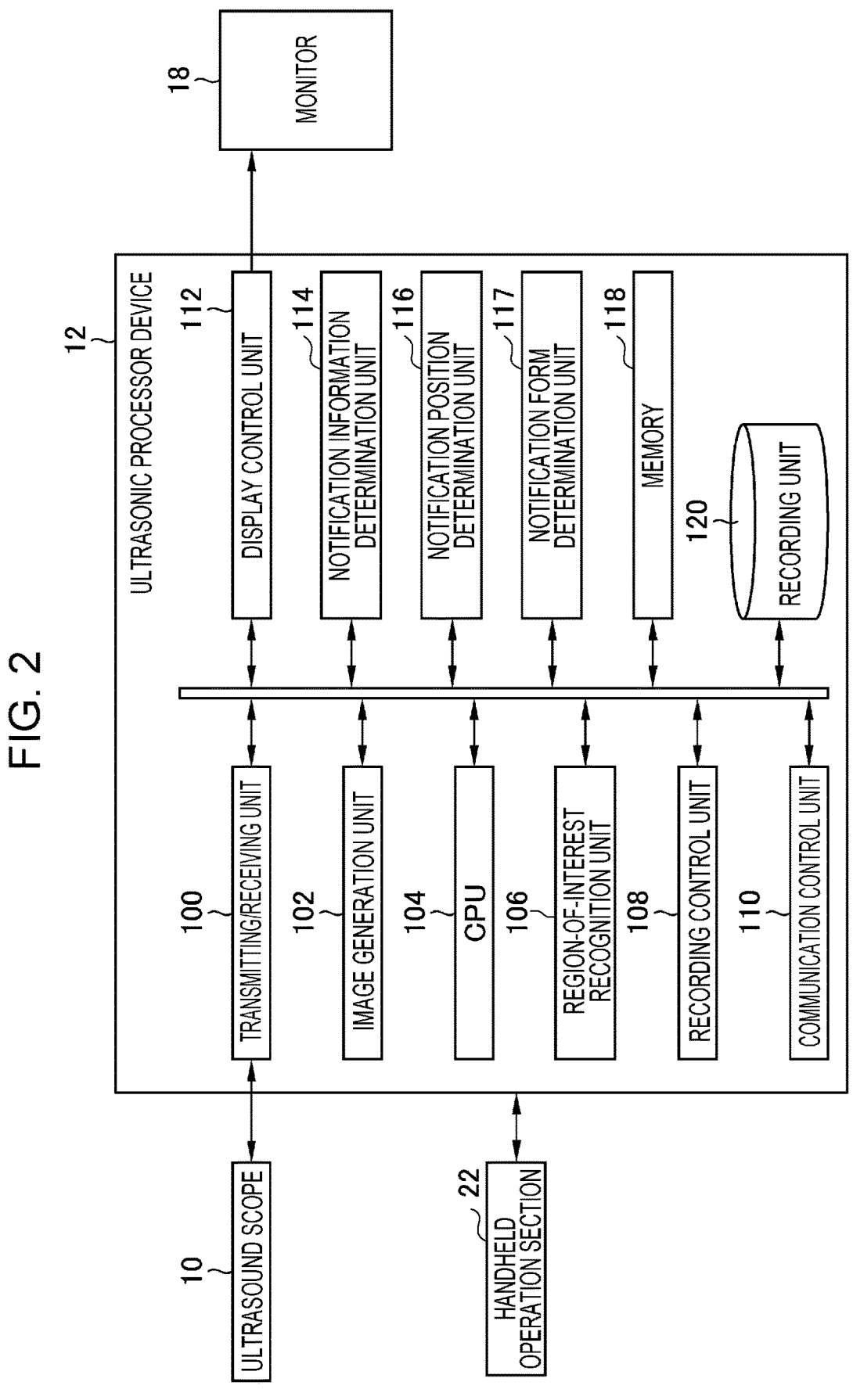

18 — MONITOR

12 — ULTRASONIC PROCESSOR DEVICE

112 — DISPLAY CONTROL UNIT

114 — NOTIFICATION INFORMATION DETERMINATION UNIT

116 — NOTIFICATION POSITION DETERMINATION UNIT

117 — NOTIFICATION FORM DETERMINATION UNIT

118 — MEMORY

120 — RECORDING UNIT

100 — TRANSMITTING/RECEIVING UNIT

102 — IMAGE GENERATION UNIT

104 — CPU

106 — REGION-OF-INTEREST RECOGNITION UNIT

108 — RECORDING CONTROL UNIT

110 — COMMUNICATION CONTROL UNIT

10 — ULTRASOUND SCOPE

22 — HANDHELD OPERATION SECTION

FIG. 4

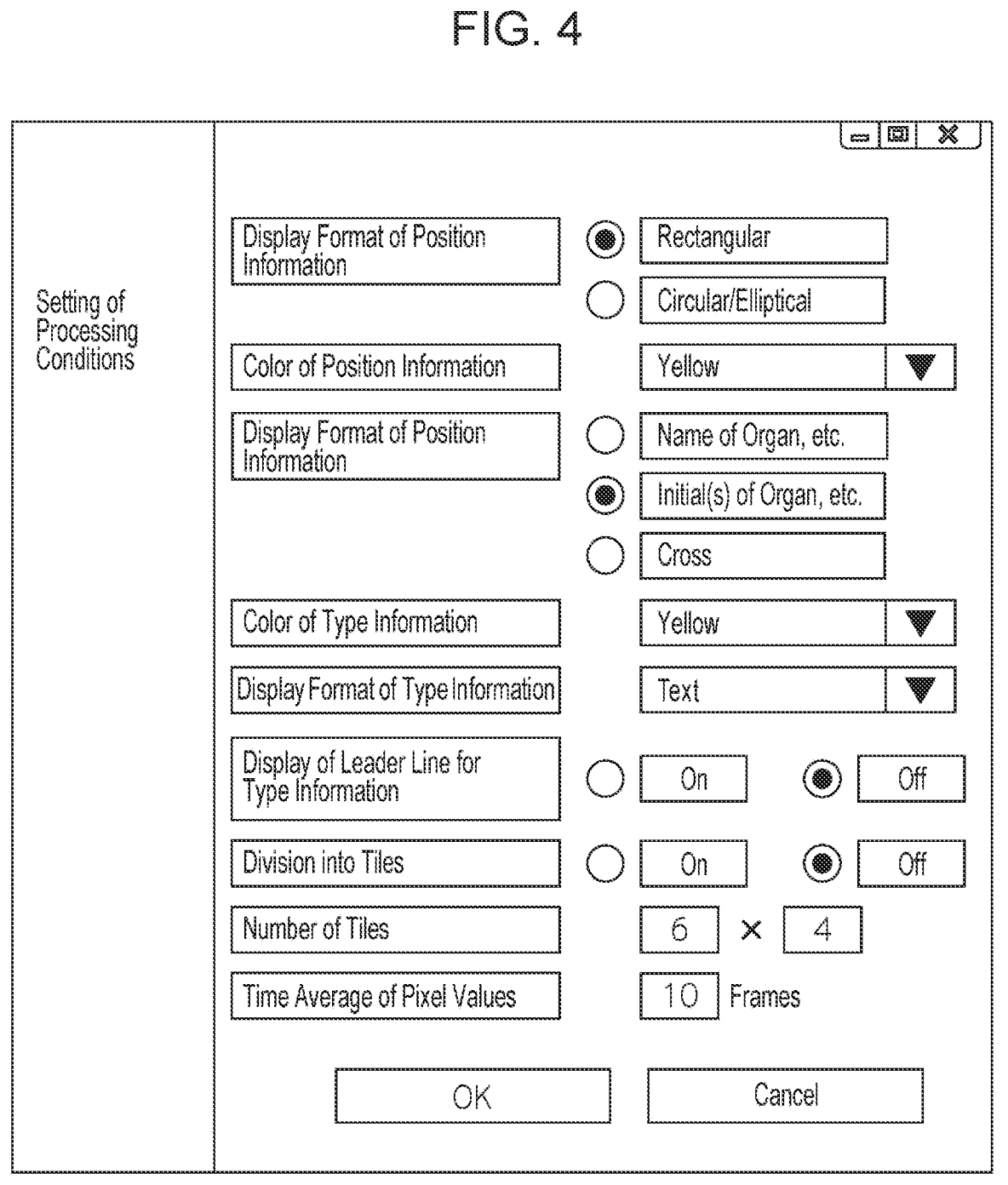

Setting of Processing Conditions

| | | |
|---|---|---|
| Display Format of Position Information | ● | Rectangular |
| | ○ | Circular/Elliptical |
| Color of Position Information | | Yellow ▼ |
| Display Format of Position Information | ○ | Name of Organ, etc. |
| | ● | Initial(s) of Organ, etc. |
| | ○ | Cross |
| Color of Type Information | | Yellow ▼ |
| Display Format of Type Information | | Text ▼ |

Display of Leader Line for Type Information    ○ On    ● Off

Division into Tiles    ○ On    ● Off

Number of Tiles    6 × 4

Time Average of Pixel Values    10 Frames

OK     Cancel

IMAGE PROCESSING APPARATUS, IMAGE PROCESSING SYSTEM, IMAGE PROCESSING METHOD, AND IMAGE PROCESSING PROGRAM

CROSS-REFERENCE TO RELATED APPLICATIONS

The present application is a Continuation of PCT International Application No. PCT/JP2022/014345 filed on Mar. 25, 2022 claiming priority under 35 U.S.C § 119(a) to Japanese Patent Application No. 2021-079511 filed on May 10, 2021. Each of the above applications is hereby expressly incorporated by reference, in its entirety, into the present application.

BACKGROUND OF THE INVENTION

1. Field of the Invention

The present invention relates to an image processing apparatus, an image processing system, an image processing method, and an image processing program, and more specifically to a technique for providing a notification of a recognition result of a region of interest.

2. Description of the Related Art

It is known to notify a user of a recognition result of a region of interest to support the user in image observation or diagnosis. For example, WO18/221033A describes the use of a bounding box or an icon to notify the user of a region of interest recognized in an image. JP2020-146202A also describes superimposed display of a bounding box.

SUMMARY OF THE INVENTION

The notification of a recognition result is expected to be used for observation or diagnosis, but may rather interfere with the user's observation or diagnosis depending on the notification method. It is therefore desirable that the position and content of a recognition result to be notified be appropriate. However, existing techniques as in WO18/221033A and JP2020-146202A, described above, do not fully consider such circumstances.

The present invention has been made in view of such circumstances, and an object thereof is to provide an image processing apparatus, an image processing system, an image processing method, and an image processing program that enable appropriate notification of a recognition result of a region of interest.

To achieve the object described above, an image processing apparatus according to a first aspect of the present invention is an image processing apparatus including a processor. The processor is configured to execute an image acquisition process for acquiring an image, a recognition process for recognizing a region of interest from the image, a notification information determination process for determining first notification information indicating a position of the region of interest in the image and second notification information indicating a type of the region of interest, and a notification position determination process for determining a notification position at which a notification of the second notification information is to be presented in the image, on the basis of pixel values in an area surrounding the region of interest in the image.

A recognition result is notified to a user by, typically, filling an entire recognition target (region of interest) with a desired color. Enclosing the entire recognition target in a rectangular or circular shape is also being studied as a notification method. At the same time, the user is also notified of the recognized object via text or an icon. Such a notification using text or an icon is being studied. In such notifications, however, when more recognition targets are notified to the user, the amount of notification increases and may impede the user's understanding. In addition, when advanced observation is required, preferably, a notification of information used for notification (such as the rectangular shape, the circular shape, the text, or the icon described above) is presented in an area having a small effect on the observation.

In view of such circumstances, the image processing apparatus according to the first aspect can present a notification of a recognition result of a region of interest at an appropriate notification position (for example, a notification position having a small effect on observation without impeding the user's understanding) on the basis of pixel values in an area surrounding the region of interest in an image. The phrase "on the basis of pixel values" refers to using the pixel values directly or using a value obtained by subjecting the pixel values to statistical processing (such as maximum values, minimum values, and averages in a determined area).

In the first aspect, the term "region of interest (ROI)" refers to a photographic subject of a specific type appearing in an image or a region of the photographic subject having a specific feature. The object to be set as the region of interest may differ depending on the type of the image or the purpose of using the image. The region of interest is also referred to as an interest region.

The "area surrounding the region of interest" may be a polygonal area such as a rectangular area, a circular area, an elliptical area, or the like. The region of interest can be recognized by using, for example, a detector implemented by machine learning such as deep learning.

The image processing apparatus according to the first aspect can be implemented as, for example, a processor portion of an image processing system, but is not limited to this aspect.

An image processing apparatus according to a second aspect is the image processing apparatus according to the first aspect, in which the processor is configured to, in the notification position determination process, determine the notification position on the basis of the type of the region of interest. An appropriate notification position may differ depending on the type of the region of interest. In the second aspect, the notification position is determined on the basis of the type of the region of interest.

An image processing apparatus according to a third aspect is the image processing apparatus according to the first or second aspect, in which the processor is configured to, in the notification position determination process, determine a center of gravity of the region of interest as the notification position.

An image processing apparatus according to a fourth aspect is the image processing apparatus according to any one of the first to third aspects, in which the processor is configured to, in the recognition process, calculate probability information indicating a certainty of recognition of the region of interest; and, in the notification position determination process, determine the notification position on the basis of the pixel values and the probability information. In the fourth aspect, a notification position can be determined in an area where the certainty of recognition of the region of interest falls within a specific range (for example, greater than or equal to a threshold value). Alternatively, the probability information can be calculated by, for example, a recognizer implemented by machine learning such as deep learning.

An image processing apparatus according to a fifth aspect is the image processing apparatus according to the fourth aspect, in which the processor is configured to acquire time-series images in the image acquisition process; and, in the notification position determination process, determine the notification position on the basis of a change over time in the probability information in the time-series images. The probability information (the certainty of recognition of the region of interest) can change with a change in ambient light, a change in observation position or direction, movement or deformation of the region of interest itself, or the like. According to the fifth aspect, an appropriate notification position can be determined in accordance with a change over time in the probability information.

In the fifth aspect and other aspects described below, the phrase "to acquire time-series images" includes acquiring a plurality of images captured at a determined frame rate. The acquisition may or may not be performed in real time. For example, images captured and recorded in advance may be acquired.

An image processing apparatus according to a sixth aspect is the image processing apparatus according to any one of the first to fourth aspects, in which the processor is configured to acquire time-series images in the image acquisition process; and, in the notification position determination process, determine the notification position on the basis of a change over time in the pixel values in the time-series images.

An image processing apparatus according to a seventh aspect is the image processing apparatus according to the fifth aspect, in which the processor is configured to, in the notification position determination process, determine the notification position on the basis of a change over time in the pixel values in the time-series images.

An image processing apparatus according to an eighth aspect is the image processing apparatus according to any one of the first to seventh aspects, in which the processor is configured to further execute a notification form determination process for determining a notification form of the second notification information. The notification form indicates, for example, which of text, a geometric shape, and a symbol to use to provide a notification, what color to use, whether to superimpose the notification, or the like.

An image processing apparatus according to a ninth aspect is the image processing apparatus according to the eighth aspect, in which the processor is configured to acquire time-series images in the image acquisition process; and, in the notification form determination process, determine the notification form on the basis of a change over time in the pixel values in the time-series images.

An image processing apparatus according to a tenth aspect is the image processing apparatus according to the eighth aspect, in which the processor is configured to acquire time-series images in the image acquisition process; in the notification position determination process, determine the notification position on the basis of a change over time in a size of the region of interest in the time-series images; and, in the notification form determination process, determine the notification form on the basis of a change over time in the size of the region of interest in the time-series images. The size of the region of interest in the images may change with a change in observation position or direction, deformation of the region of interest itself, or the like. If the size changes, the appropriate notification position or notification form of the second notification information (type information) may also change. In the tenth aspect, accordingly, a notification position and a notification form are determined on the basis of a change in the size of the region of interest over time.

An image processing apparatus according to an eleventh aspect is the image processing apparatus according to the ninth aspect, in which the processor is configured to, in the notification position determination process, determine the notification position on the basis of a change over time in a size of the region of interest in the time-series images; and, in the notification form determination process, determine the notification form on the basis of a change over time in the size of the region of interest in the time-series images. In the eleventh aspect, as in the tenth aspect, a notification position and a notification form are determined on the basis of a change in the size of the region of interest over time.

An image processing apparatus according to a twelfth aspect is the image processing apparatus according to any one of the first to eleventh aspects, in which the processor is configured to superimpose the first notification information and the second notification information on the image and record the superimposed first notification information and second notification information in a recording device.

An image processing apparatus according to a thirteenth aspect is the image processing apparatus according to any one of the first to twelfth aspects, in which the processor is configured to record the second notification information and/or the notification position in a recording device.

An image processing apparatus according to a fourteenth aspect is the image processing apparatus according to any one of the first to thirteenth aspects, in which the processor is configured to acquire a medical image of a subject in the image acquisition process. In the present invention, the term "medical image" refers to an image obtained as a result of imaging, measurement, or the like of a living body such as a human body for the purpose of diagnosis, treatment, measurement, or the like, and examples thereof include an endoscopic image, an ultrasound image, a CT image (CT: Computed Tomography), and an MRI image (MRI: Magnetic Resonance Imaging). The medical image is also referred to as an image for medical use. In the case of a medical image, the region of interest may be a lesion region or a candidate lesion region, an organ or a vessel, a region after treatment, or an instrument such as a treatment tool.

To achieve the object described above, an image processing system according to a fifteenth aspect of the present invention includes the image processing apparatus according to any one of the first to fourteenth aspects, and an imaging device that captures the image. The image processing system according to the fifteenth aspect includes the image processing apparatus according to any one of the first to fourteenth aspects, and thus can appropriately display a recognition result of a region of interest.

An image processing system according to a sixteenth aspect is the image processing system according to the fifteenth aspect, in which the imaging device is an endoscope. According to the sixteenth aspect, an image of the inside of a lumen-shaped target object can be acquired with the endoscope.

An image processing system according to a seventeenth aspect is the image processing system according to the sixteenth aspect, in which the endoscope is an ultrasonic endoscope. According to the seventeenth aspect, an ultrasound image of a target object can be acquired with the ultrasonic endoscope.

An image processing system according to an eighteenth aspect is the image processing system according to any one of the fifteenth to seventeenth aspects, in which the processor is configured to cause a display device to display the image, the first notification information, and the second notification information in a superimposed manner. According to the eighteenth aspect, the user can easily visually grasp the position information and the type information of the region of interest.

An image processing system according to a nineteenth aspect is the endoscope system according to the eighteenth aspect, further including the display device.

To achieve the object described above, an image processing method according to a twentieth aspect of the present invention is an image processing method executed by an image processing apparatus including a processor, the processor being configured to execute an image acquisition step of acquiring an image, a recognition step of recognizing a region of interest from the image, a notification information determination step of determining first notification information indicating a position of the region of interest in the image and second notification information indicating a type of the region of interest, and a notification position determination step of determining a notification position at which a notification of the second notification information is to be presented in the image, on the basis of pixel values in an area surrounding the region of interest in the image.

The twentieth aspect enables appropriate notification of a recognition result of the region of interest, as in the first aspect. The image processing method according to the twentieth aspect may further execute processes similar to those according to the second to fourteenth aspects.

To achieve the object described above, an image processing program according to a twenty-first aspect of the present invention is an image processing program for causing an image processing apparatus including a processor to execute an image processing method. The image processing method includes an image acquisition step of acquiring an image, a recognition step of recognizing a region of interest from the image, a notification information determination step of determining first notification information indicating a position of the region of interest in the image and second notification information indicating a type of the region of interest, and a notification position determination step of determining a notification position at which a notification of the second notification information is to be presented in the image, on the basis of pixel values in an area surrounding the region of interest in the image.

The twenty-first aspect enables appropriate notification of a recognition result of the region of interest, as in the first and twentieth aspects. The image processing program according to the twenty-first aspect may be a program for further executing processes similar to those according to the second to fourteenth aspects. Aspects of the present invention can also provide a non-transitory recording medium storing computer-readable code of the program according to these aspects.

As described above, an image processing apparatus, an image processing system, an image processing method, and an image processing program according to the present invention enable appropriate notification of a recognition result of a region of interest.

BRIEF DESCRIPTION OF THE DRAWINGS

FIG. 2 is a block diagram illustrating a configuration of a main part of an ultrasonic processor device;

FIG. 4 is a view illustrating an example of a setting screen of a notification form;

DESCRIPTION OF THE PREFERRED EMBODIMENTS

Embodiments of an image processing apparatus, an image processing system, an image processing method, and an image processing program according to the present invention will be described in detail hereinafter with reference to the accompanying drawings.

First Embodiment

Overall Configuration of Endoscope System Including Image Processing Apparatus

Figure 1:
FIG. 1 is an external view of an endoscope system according to a first embodiment.

FIG. 1 is an external view of an endoscope system according to a first embodiment. As illustrated in FIG. 1, an endoscope system 2 (image processing system or endoscope system) includes an ultrasound scope 10 (endoscope, ultrasonic endoscope, or imaging device), an ultrasonic processor device 12 (image processing apparatus, processor, or imaging device) that generates an ultrasound image (medical image), an endoscope processor device 14 (image processing apparatus) that generates an endoscopic image (medical image), a light source device 16 that supplies illumination light (observation light) to the ultrasound scope 10 to illuminate the inside of a body cavity, and a monitor 18 (display device) that displays the ultrasound image and the endoscopic image.

The ultrasound scope 10 includes an insertion section 20 to be inserted into a body cavity of a subject, a handheld operation section 22 coupled to a proximal end portion of the insertion section 20 and to be operated by an operator, and a universal cord 24 having one end connected to the handheld operation section 22. The other end of the universal cord 24 is provided with an ultrasonic connector 26 to be connected to the ultrasonic processor device 12, an endoscope connector 28 to be connected to the endoscope processor device 14, and a light source connector 30 to be connected to the light source device 16.

The ultrasound scope 10 is detachably connected to the ultrasonic processor device 12, the endoscope processor device 14, and the light source device 16 through these connectors. The light source connector 30 is also connected to an air/water supply tube 32 and a suction tube 34.

The light source device 16 is constituted by light sources for illumination (for example, a red light source, a green light source, a blue light source, and a violet light source that emit red, green, blue, and violet narrow-band light, respectively), a diaphragm, a condenser lens, a light source control unit, and so on, and these light sources can convert normal light (white light), special light (such as narrow-band light), and a combination thereof into observation light.

The monitor 18 receives respective video signals generated by the ultrasonic processor device 12 and the endoscope processor device 14 and displays an ultrasound image and an endoscopic image. The ultrasound image and the endoscopic image can be displayed such that only one of the images is appropriately switched and displayed on the monitor 18, or both of the images are simultaneously displayed.

The handheld operation section 22 is provided with an air/water supply button 36 and a suction button 38, which are arranged side by side, and is also provided with a pair of angle knobs 42 and a treatment tool insertion port 44.

The insertion section 20 has a distal end, a proximal end, and a longitudinal axis 20a. The insertion section 20 is constituted by a tip main body 50, a bending part 52, and an elongated long flexible soft part 54 in this order from the distal end side of the insertion section 20. The tip main body 50 is formed by a hard member. The bending part 52 is coupled to the proximal end side of the tip main body 50. The soft part 54 couples the proximal end side of the bending part 52 to the distal end side of the handheld operation section 22. That is, the tip main body 50 is disposed on the distal end side of the insertion section 20 in the direction of the longitudinal axis 20a. The bending part 52 is operated to bend by turning the pair of angle knobs 42 disposed in the handheld operation section 22. As a result, the user can direct the tip main body 50 in a desired direction.

The tip main body 50 is attached with an ultrasound probe 62 (imaging device or imaging unit) and a bag-like balloon 64 that covers the ultrasound probe 62. The balloon 64 can expand or contract when water is supplied from a water supply tank 70 or the water in the balloon 64 is sucked by a suction pump 72. The balloon 64 is inflated until the balloon 64 abuts against the inner wall of the body cavity to prevent attenuation of an ultrasound wave and an ultrasound echo (echo signal) during ultrasound observation.

The tip main body 50 is also attached with an endoscopic observation portion (not illustrated) having an illumination portion and an observation portion including an objective lens, an imaging element, and so on. The endoscopic observation portion is disposed behind the ultrasound probe 62 (on the handheld operation section 22 side).

With the configuration described above, the endoscope system 2 can acquire (capture) an endoscopic image (optical image) and an ultrasound image. The endoscope system 2 may acquire an endoscopic image or an ultrasound image from a recording unit 120 or a server or a database (not illustrated).

Image Processing Apparatus

FIG. 2 is a diagram illustrating a configuration of a main part of an ultrasonic processor device.

The ultrasonic processor device 12 (image processing apparatus, processor, or imaging device) illustrated in FIG. 2 is a device that recognizes a region of interest (target object) in a medical image on the basis of acquired time-series medical images and displays (provides a notification of) a recognition result on a display device, and is constituted by a transmitting/receiving unit 100 (processor or image acquisition unit), an image generation unit 102 (processor or image acquisition unit), a CPU 104 (processor or image acquisition unit), a region-of-interest recognition unit 106 (processor or recognition unit), a recording control unit 108 (processor or recording control unit), a communication control unit 110 (processor), a display control unit 112 (processor or display control unit), a memory 118 (memory), and a recording unit 120 (recording device or memory). The processes of these components is implemented by one or more processors, as described below.

The CPU 104 operates in accordance with various programs stored in the memory 118 or the recording unit 120 and including an image processing program according to the present invention to perform overall control of the region-of-interest recognition unit 106, the recording control unit 108, the communication control unit 110, the display control unit 112, a notification information determination unit 114, a notification position determination unit 116, and a notification form determination unit 117, and functions as some of these components. The memory 118 includes a non-transitory recording medium such as a ROM (ROM: Read Only Memory) in which the image processing program according to the present invention and the like are recorded, and a transitory recording medium such as a RAM (RAM: Random Access Memory) used as a temporary storage area.

The transmitting/receiving unit 100 and the image generation unit 102, which function as an image acquisition unit, acquire time-series medical images (image acquisition process or image acquisition step).

A transmitting unit of the transmitting/receiving unit 100 generates a plurality of drive signals to be applied to a plurality of ultrasonic transducers of the ultrasound probe 62 of the ultrasound scope 10, assigns respective delay times to the plurality of drive signals on the basis of a transmission delay pattern selected by a scan control unit (not illustrated), and applies the plurality of drive signals to the plurality of ultrasonic transducers.

A receiving unit of the transmitting/receiving unit 100 amplifies a plurality of detection signals, each of which is output from one of the plurality of ultrasonic transducers of the ultrasound probe 62, and converts the detection signals from analog detection signals to digital detection signals (also referred to as RF (Radio Frequency) data). The RF data is input to the image generation unit 102.

The image generation unit 102 assigns respective delay times to the plurality of detection signals represented by the RF data on the basis of a reception delay pattern selected by the scan control unit and adds the detection signals together to perform reception focus processing. Through the reception focus processing, sound ray data in which the focus of the ultrasound echo is narrowed is formed.

The image generation unit 102 corrects the sound ray data for attenuation caused by the distance in accordance with the depth of the reflection position of the ultrasound wave by using STC (Sensitivity Time Control), and then performs envelope detection processing on the corrected sound ray data by using a low pass filter or the like to generate envelope data. The image generation unit 102 stores envelope data for one frame or more preferably for a plurality of frames in a cine memory (not illustrated). The image generation unit 102 performs pre-process processing, such as Log (logarithmic) compression and gain adjustment, on the envelope data stored in the cine memory to generate a B-mode image.

In this way, the transmitting/receiving unit 100 and the image generation unit 102 acquire time-series B-mode images (hereafter referred to as "medical images").

The region-of-interest recognition unit 106 performs a process (detection process/detection step and recognition process/recognition step) for recognizing information related to the position of a region of interest in a medical image on the basis of the medical images and a process (classification process/classification step and recognition process/recognition step) for classifying the region of interest into a class among a plurality of classes on the basis of the medical image. The region-of-interest recognition unit 106 can be configured using a trained model (a model trained by using an image set constituted by captured images of a living body) implemented by machine learning, such as a CNN (Convolutional Neural Network), an SVM (Support Vector Machine), or a U-net (type of FCN (Fully Convolution Network)). In the present embodiment, the region of interest is, for example, an organ or a blood vessel in a medical image (a tomographic image of a B-mode image), and examples of the region of interest include the pancreas, the main pancreatic duct, the spleen, the splenic vein, the splenic artery, and the gallbladder.

An example of a layer configuration of a CNN by which the region-of-interest recognition unit 106 is configured will be described. The CNN includes an input layer, an intermediate layer, and an output layer. The input layer receives a medical image generated by the image generation unit 102 and outputs a feature value. The intermediate layer includes convolution layers and pooling layers and receives the feature value output from the input layer to calculate another feature value. These layers have a structure in which a plurality of "nodes" are connected by "edges", and hold a plurality of weight parameters. The values of the weight parameters change as learning progresses. The output layer recognizes a region of interest appearing in the input medical image on the basis of the feature value output from the intermediate layer and outputs the result.

In this example, when receiving time-series medical images, the region-of-interest recognition unit 106 recognizes (detects) the position of a region of interest for each of the received medical images, outputs information indicating the position (position information or first notification information), recognizes (classifies) a class (type) to which the region of interest belongs among a plurality of classes, and outputs information (class information, type information, or second notification information) indicating the recognized class (type). In the recognition, the region-of-interest recognition unit 106 can output information (probability information) indicating the certainty of recognition of the region of interest. For example, it is possible to calculate the probability that each pixel of the medical image is a region of interest or the probability that the region of interest belongs to a predetermined class (for example, the pancreas, the main pancreatic duct, the spleen, the splenic vein, the splenic artery, the gallbladder, or the like). The region-of-interest recognition unit 106 can calculate such a probability on the basis of, for example, the output of the output layer of the CNN.

The display control unit 112 causes the monitor 18 (display device) to display the time-series medical images (endoscopic images and ultrasound images) acquired by the transmitting/receiving unit 100 and the image generation unit 102. In this example, a moving image indicating an ultrasound tomographic image is displayed on the monitor 18. Further, the display control unit 112 causes the monitor 18 to display the region of interest in the medical image in the position, type, form, and the like determined by the notification information determination unit 114, the notification position determination unit 116, and the notification form determination unit 117. The notification information determination unit 114 (processor or notification information determination unit) determines notification information (first notification information and second notification information) related to the region of interest. The notification position determination unit 116 (processor or notification position determination unit) determines a notification position of the second notification information. The notification form determination unit 117 (processor or notification form determination unit) determines a notification form of the second notification information.

Image processing using the functions described above will be described in detail below.

Implementation of Functions by Various Processors

The functions of the ultrasonic processor device 12 described above can be implemented using various processors and a recording medium. The various processors include, for example, a CPU (Central Processing Unit), which is a general-purpose processor that executes software (program) to implement various functions. The various processors described above also include a GPU (Graphics Processing Unit), which is a processor specialized for image processing, and a programmable logic device (PLD) such as an FPGA (Field Programmable Gate Array), which is a processor whose circuit configuration is changeable after manufacture. A configuration using a GPU is effective for the processing of images as in the present invention. Further, a dedicated electric circuit or the like, which is a processor having a circuit configuration designed specifically for executing specific processing, such as an ASIC (Application Specific Integrated Circuit), is also included in the "various processors" described above.

The function of each component may be implemented by one processor or may be implemented by a plurality of processors of the same type or different types (for example, a plurality of FPGAs, a combination of a CPU and an FPGA, or a combination of a CPU and a GPU). Alternatively, a plurality of functions may be implemented by a single processor. Examples of configuring a plurality of functions by a single processor include, first, a form in which, as typified by a computer, the single processor is configured by a combination of one or more CPUs and software and the processor is implemented as the plurality of functions. The examples include, second, a form in which, as typified by a system on chip (SoC) or the like, a processor is used in which the functions of the entire system are implemented by a single IC (Integrated Circuit) chip. As described above, the various functions are configured using one or more of the various processors described above as a hardware structure. More specifically, the hardware structure of the various processors is an electric circuit (circuitry) including a combination of circuit elements such as semiconductor elements. These electric circuits may be electric circuits that implement the functions described above by using logical operations such as logical OR, logical AND, logical NOT, exclusive OR, and a combination thereof.

When the processor or electric circuit described above executes software (program), the code of the software to be executed, which is readable by a computer (for example, various processors or electric circuits constituting the ultrasonic processor device 12, and/or a combination thereof), is stored in a non-transitory recording medium such as a ROM (Read Only Memory), and the computer refers to the software. The software stored in the non-transitory recording medium includes an image processing program for executing an image processing method according to the present invention, and data used for the execution (such as data used to set a display style and a notification style, and weight parameters used by the region-of-interest recognition unit 106). The code may be recorded in a non-transitory recording medium such as various magneto-optical recording devices or a semiconductor memory, instead of the ROM. At the time of processing using software, for example, a RAM (RAM: Random Access Memory, or memory) is used as a temporary storage area, and, for example, data stored in an EEPROM (Electrically Erasable and Programmable Read Only Memory) (not illustrated) can also be referred to. The "non-transitory recording medium" may be the memory 118 or the recording unit 120.

The recording unit 120 has recorded thereon an ultrasound image and an endoscopic image (medical image), a detection result of a region of interest, processing conditions (conditions for detection and notification), and so on. Other information may also be recorded. The communication control unit 110 performs control to acquire a medical image and the like from another medical imaging apparatus, an external server, or a database connected to the endoscope system 2. The recording control unit 108 performs recording control on the recording unit 120. The recording control includes recording of notification information (first notification information and second notification information), a notification position, a notification form, an image obtained by superimposing the notification information on an ultrasound image or an endoscopic image, and the like.

Procedure of Image Processing

Figure 3:
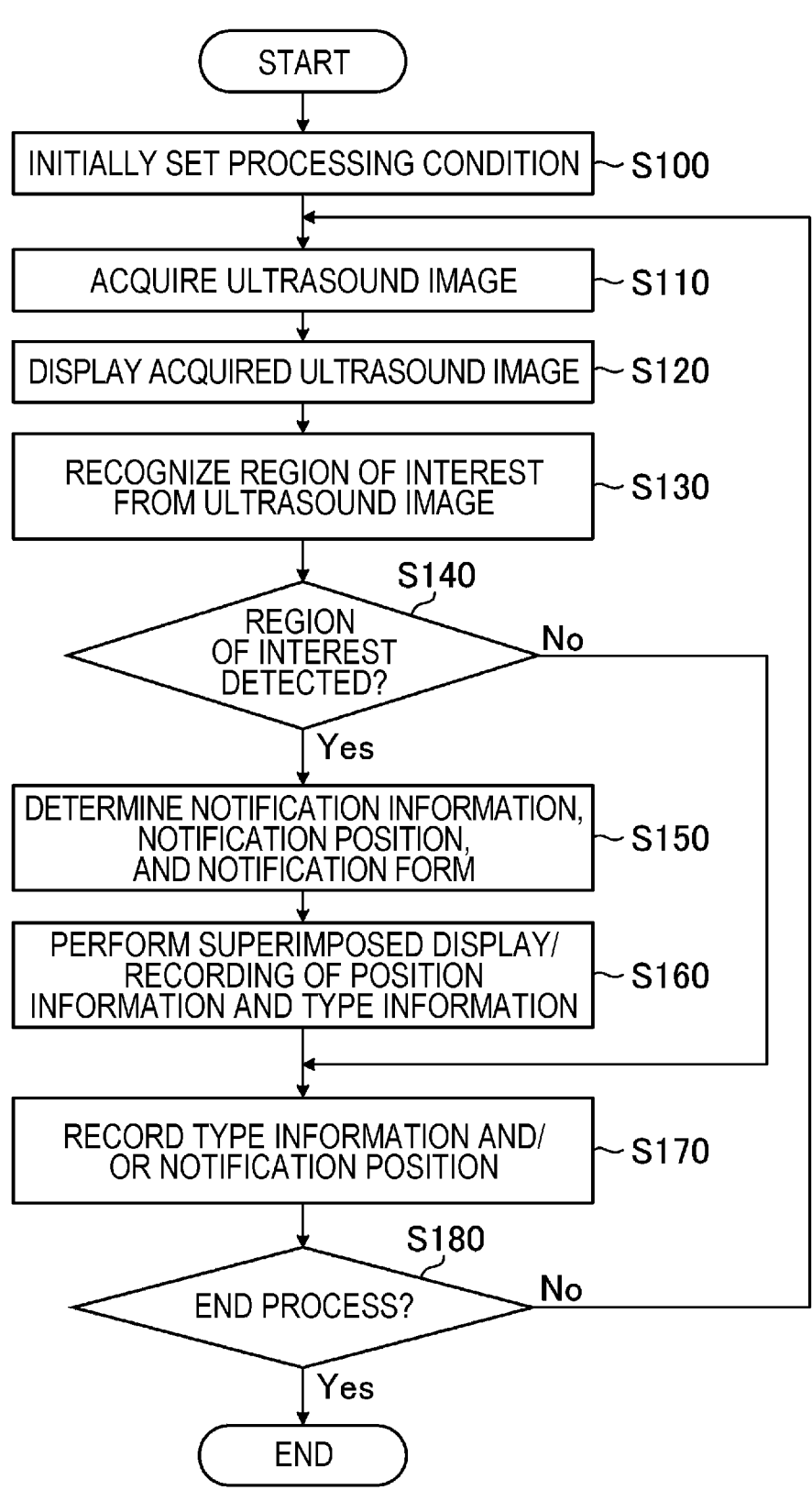
FIG. 3 is a flowchart illustrating steps of an image processing method according to the first embodiment.

Image processing (execution of the image processing method and the image processing program according to the present invention) in the endoscope system 2 having the configuration described above will be described. FIG. 3 is a flowchart illustrating steps of an image processing method according to the first embodiment. The steps described below may be executed in a different order as necessary.

1. Setting of Processing Conditions

The display control unit 112 (processor) sets conditions necessary to execute the image processing method/image processing program in accordance with the user's operation through an operation section (such as a keyboard, a mouse, a touch panel, or a microphone) (not illustrated) and/or preset processing conditions (for example, default processing conditions) (step S100: processing condition setting step). For example, the display control unit 112 sets the display style (such as the type and color of a text or a symbol) of the position information and the type information, the presence or absence of a leader line for the type information, the presence or absence of tile division, the number of time-average frames of pixel values, and so on. For example, the user can set the processing conditions on a screen such as that in FIG. 4 (not all of the settings for the processing conditions are illustrated) by, for example, turning on/off a radio button, making a selection in a pull-down menu, or inputting a numerical value through the operation section. The display control unit 112 can cause a display device such as the monitor 18 to display such a screen. The settings include, for example, what kind of geometric shape or text (such as the type and color) to use to display the position information and the type information. The display control unit 112 may set the processing conditions not only at the start of processing but also during the execution of the following steps.

2. Acquisition of Ultrasound Image and Recognition of Region of Interest

The transmitting/receiving unit 100 and the image generation unit 102 acquire time-series ultrasound images (medical images) (step S110: image acquisition process or image acquisition step). The display control unit 112 causes the monitor 18 to display an acquired ultrasound image (step S120: display control process or display control step). The region-of-interest recognition unit 106 recognizes the position and type of a region of interest in the ultrasound image (step S130: recognition process or recognition step). The region-of-interest recognition unit 106 can identify, for example, the center position of a rectangular shape, a circular shape, or an elliptical shape (which can be set in the "display format of position information" field in FIG. 4) surrounding the region of interest as the "position of the region of interest", and identify information indicating the position (such as coordinates in the image) as the "first notification information". In the present embodiment, information (class information or type information) indicating the type of the region of interest such as an organ or a blood vessel can be identified as the "second notification information". In the following, the "first notification information" may be referred to as "position information", and the "second notification information" may be referred to as "type information".

3. Determination of Notification Information, Notification Position, and Notification Form If the region-of-interest recognition unit 106 detects a region of interest (YES in step S140), notification information, a notification position, and a notification form are determined in the following way (step S150: notification information determination process/notification information determination step and notification position determination process/notification position determination step). These processes or steps may be performed on each frame of the ultrasound image, or may be performed on the basis of a change over time in various parameters in the time-series image, as described below. Alternatively, the processes or steps may be performed on the basis of pixel values in a plurality of areas into which an image is segmented.

3.1 Determination of Notification Information

The notification information determination unit 114 determines the first notification information indicating the position of the region of interest in the ultrasound image (medical image) and the second notification information indicating the type of the region of interest (step S150: notification information determination process or notification information determination step). The notification information determination unit 114 can identify the center of gravity of pixels recognized as being in the "region of interest" by the region-of-interest recognition unit 106 or the minimum values/maximum values or the like of the X coordinate and the Y coordinate as "(information indicating) the position of the region of interest". The notification information determination unit 114 can further identify the classification result of the region of interest (such as the name of an organ or a vessel (such as the pancreas, the splenic vein, or the portal vein), a lesion region, or a region after treatment) obtained by the region-of-interest recognition unit 106 as the "type of the region of interest".

3.2(1) Determination of Notification Position of Type Information

The notification position determination unit 116 determines, based on pixel values in an area surrounding the region of interest in the ultrasound image (medical image), a notification position at which a notification of the type information (second notification information) of the region of interest is to be presented in the image (notification position determination process or notification position determination step). For example, the notification position determination unit 116 can determine, as the "notification position of the type information", the center of gravity of an area having pixel values greater than or equal to a threshold value or the center of gravity of an area having pixel values less than a threshold value. The notification position determination unit 116 may determine a position other than the center of gravity as the notification position, or may present a notification of the type information of a certain region of interest in a location outside the region of interest (see example displays described below with reference to FIGS. 5 to 8). The "area surrounding the region of interest" may have any shape such as a rectangular shape, a polygonal shape, a circular shape, or an elliptical shape (illustrated as the "display format of position information" in the example in FIG. 4).

The notification position determination unit 116 may determine the notification position of the type information on the basis of the type of the region of interest. For example, when the region of interest is the pancreas, the notification position determination unit 116 can determine the notification position in an area other than an area such as the vascular system having low echo values (pixel values). When the region of interest is the vascular system, conversely, the notification position determination unit 116 can search for an area having low echo values to determine the notification position.

3.2(2) Determination of Notification Position Based on Probability Information

The notification position determination unit 116 (processor) may calculate probability information indicating the certainty of recognition of the region of interest and determine the notification position on the basis of the pixel values and the probability information. For example, the notification position determination unit 116 can determine, as the notification position, the center of gravity of a pixel whose pixel value such as an echo value is greater than or equal to a reference value and whose probability of belonging to a specific type of region of interest is greater than or equal to a reference value. For example, the region-of-interest recognition unit 106 can calculate the probability information on the basis of the output of the output layer of the CNN.

3.3 Determination of Notification Form

The notification form determination unit 117 (processor) determines a notification form of the type information (second notification information) (notification form determination process or notification form determination step). The "notification form" indicates, for example, which of text, a geometric shape, and a symbol to use to provide a notification, what color to use, or whether to display the notification in a superimposed manner. The notification form determination unit 117 can determine the notification form in accordance with the user's operation via a setting screen as illustrated in FIG. 4.

Processing for Time-Series Images

In step S150, the notification information determination unit 114, the notification position determination unit 116, and the notification form determination unit 117 may perform processing or provide a notification on the basis of a change over time in various conditions (such as the pixel values, the size of the region of interest, and the probability information) in the time-series images acquired in the image acquisition process (image acquisition step). Specifically, the notification information determination unit 114 and the notification position determination unit 116 can determine the notification information (first notification information and second notification information) and the notification position on the basis of a change in pixel value over time, respectively, and the notification position determination unit 116 and the notification form determination unit 117 can determine the notification position and the notification form on the basis of a change over time in the size of the region of interest in the ultrasound images, respectively.

For example, when the shape or the pixel values of the region of interest change over time, the notification position may move greatly, which may cause the user to lose concentration. Thus, it is considered to present a notification at a position where the shape or the pixel values of the region of interest change as small as possible over time. The reference value in the case where a change over time is taken into account may be a time-series difference or amount of change in pixel value, or may be based on a degree of invariance of shape obtained from a recognition score or the like.

The notification position determination unit 116 may determine the notification position on the basis of a change over time in the probability information. The phrase "on the basis of a change over time", as used here, includes a state where the notification information determination unit 114, the notification position determination unit 116, and the notification form determination unit 117 take into account, for example, the average values, the maximum values, or the minimum values of various conditions over a determined period of time (the number of frames). The notification information determination unit 114, the notification position determination unit 116, and the notification form determination unit 117 can also take into account whether frames in which the values of the various conditions are greater than or equal to threshold values continue for a determined period of time (number of frames) or more.

As described above, taking into account changes over time in various conditions makes it possible to reduce the possibility that a change over time in a condition such as a pixel value or size will cause a frequent change in notification position or the like and interfere with observation, the possibility that an inappropriate notification will be provided due to incorrect recognition of the region of interest, the possibility that the notification will fail due to recognition failure, or the like. The period of time (number of frames) over which the changes over time are taken into account can be set via a screen as illustrated in FIG. 4, for example.

4. Display and Recording

The display control unit 112 (processor) determines the notification forms of the first notification information and the second notification information on the basis of the conditions set in step S100, and causes the monitor 18 (display device) to display the first notification information and the second notification information such that the first notification information and the second notification information are superimposed on the ultrasound image (step S160: display control process or display control step). Further, the recording control unit 108 (processor) records the first notification information and the second notification information, which are superimposed on the ultrasound image, in the recording unit 120 (recording device) (step S160: recording control process or recording control step). Further, the recording control unit 108 records the type information (second notification information) and/or the notification position of the type information in the recording unit 120 (step S170: recording control process or recording control step). The processing of steps S110 to S170 is repeatedly performed until YES is obtained in step S180 (this determination is YES, for example, when the user performs an operation to terminate imaging or when the process is completed for all the recorded images).

Example Notification (Example Display)

Figure 5:
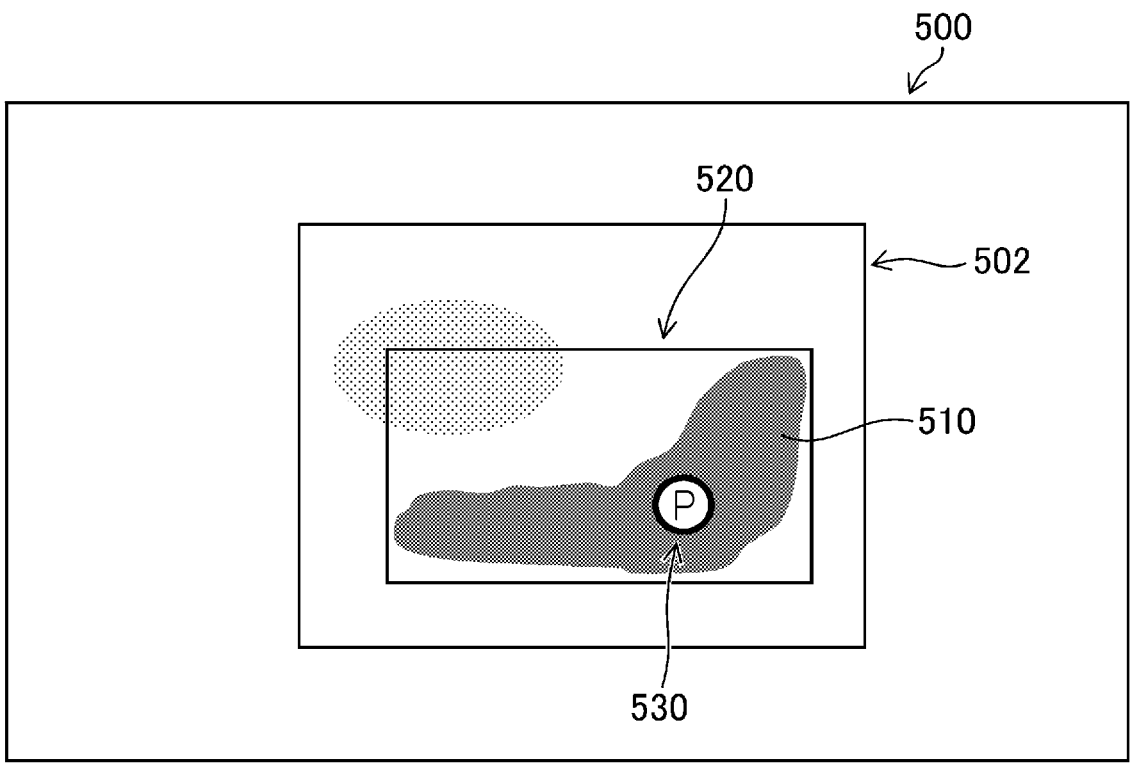
FIG. 5 is a diagram illustrating an example notification (example display) of first notification information and second notification information.

FIG. 5 is a diagram illustrating an example notification (example display) of the first notification information and the second notification information. In the example illustrated in FIG. 5, an ultrasound image 502 is displayed on a screen 500 of the monitor 18, and the display control unit 112 displays a rectangular shape 520 (bounding box or first notification information) indicating the position of a region of interest 510 and a geometric shape 530 (second notification information) indicating the type of the region of interest 510 such that the rectangular shape 520 and the geometric shape 530 are superimposed on the ultrasound image 502. The position of the region of interest 510 is the center of the rectangular shape 520, and the geometric shape 530, which uses the initial letter "P" of pancreas, indicates the type of the region of interest 510. The notification position of the geometric shape 530 (second notification information), that is, the notification position of the type of the region of interest 510, is the center of gravity of a region (illustrated in dark gray) having pixel values greater than or equal to a reference value within the rectangular shape 520, which is an area surrounding the region of interest 510. According to this aspect, the user can check the type information without greatly moving the line of sight from the region of interest. The notification position of the type of the region of interest may be determined by using pixel values in an area surrounding the region of interest and setting information of the imaging device. Examples of the setting information of the imaging device include the measurement mode (such as the B-mode or the M-mode) of the ultrasound scope 10, and the light source irradiation mode and the magnification of the endoscope. For example, the reference value described above is changed in accordance with the measurement mode of the ultrasound scope 10 or the irradiation mode of the light source device 16 of the endoscope system 2. As a result, the notification position of the type of the region of interest can be determined on the basis of the setting information of the imaging device. The notification position of the type of the region of interest is determined on the basis of the pixel values in an area surrounding the region of interest and the setting information of the imaging device, thus allowing the user to visually recognize the type information even if the brightness or contrast greatly changes due to the setting of the imaging device. The notification position of the type of the region of interest may be determined by using the setting information of the monitor 18 in addition to the pixel values in the area surrounding the region of interest.

Figure 6:
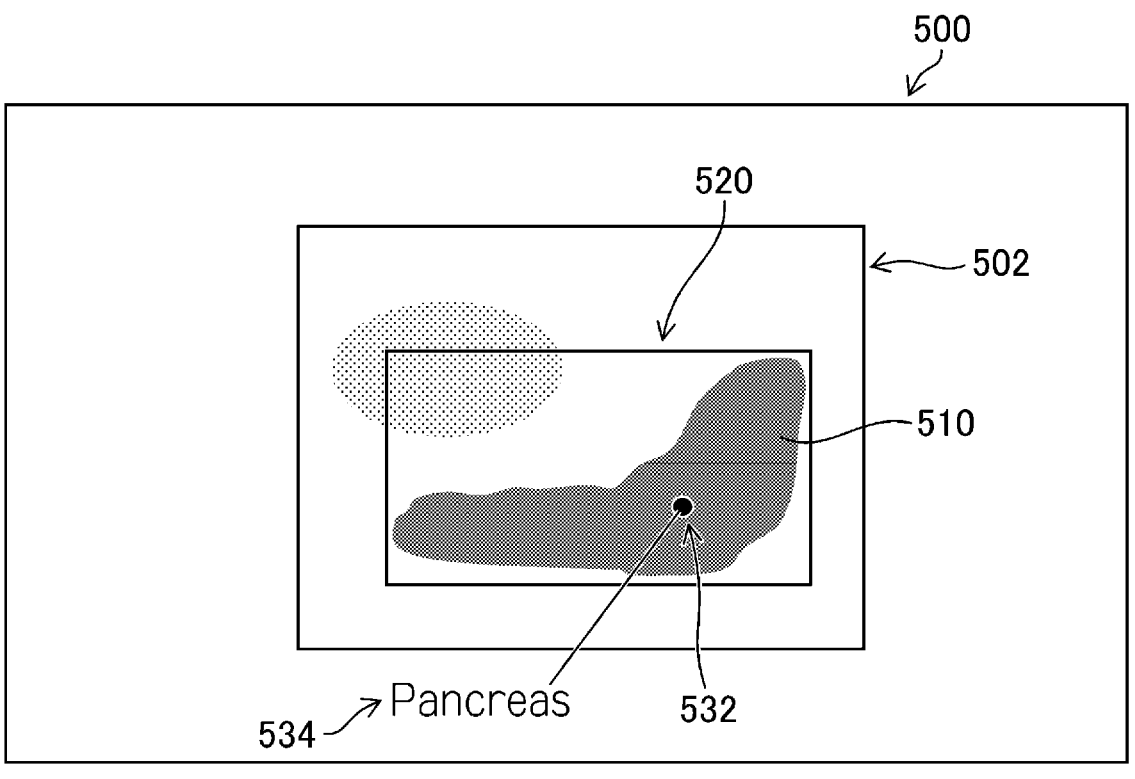
FIG. 6 is a diagram illustrating another example notification (example display) of the first notification information and the second notification information.

FIG. 6 is a diagram illustrating another example notification (example display) of the first notification information and the second notification information. In the example illustrated in FIG. 6, the display control unit 112 superimposes a symbol 532 at the center of gravity of a region illustrated in dark gray, and superimposes text 534 ("Pancreas") indicating the type information (second notification information) at an end of a leader line having another end located at the symbol 532. Displaying the text 534 outside the region of interest 510 can prevent the region of interest 510 from being hidden.

Figure 7:
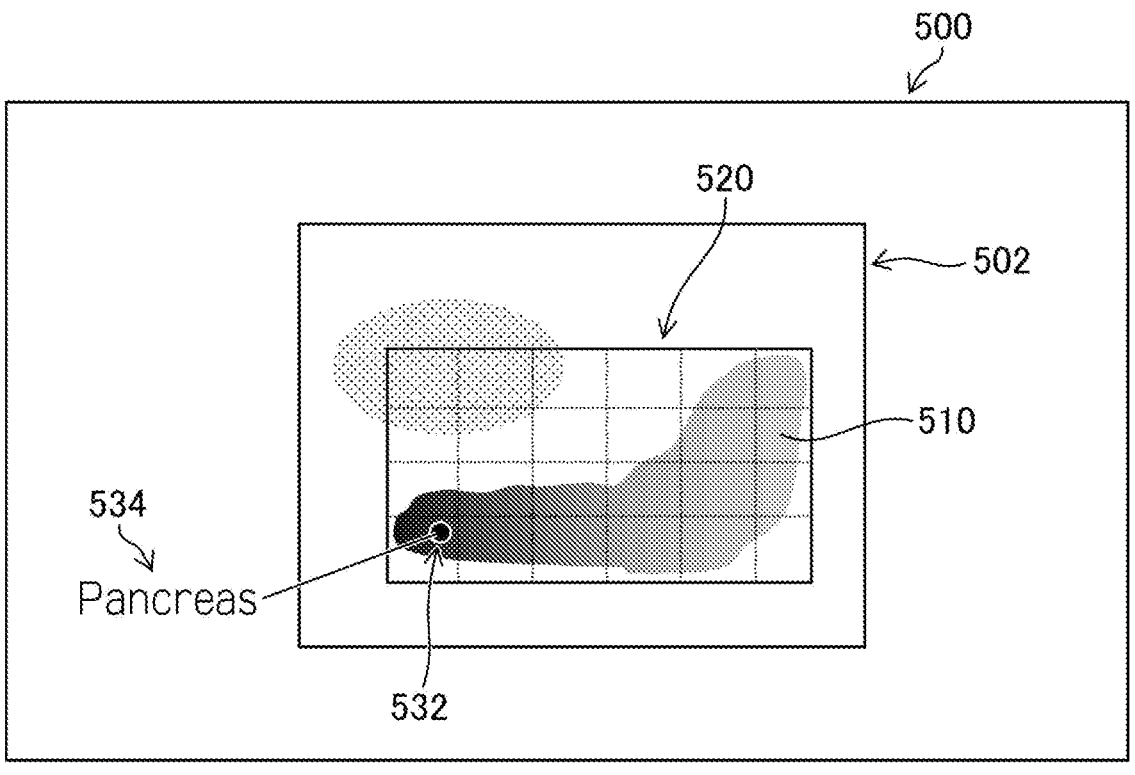
FIG. 7 is a diagram illustrating still another example notification (example display) of the first notification information and the second notification information.

In the notification of the recognition result, it is important where to display the first notification information and the second notification information. Superimposition of the notification information on the part to be observed in the region of interest may interfere with detailed observation when the detailed observation is needed. In contrast, presenting the notification across the outside of the region of interest may make the user confused because the user does not understand in which portion the notification information indicates a recognition result. Accordingly, preferably, the notification position determination unit 116 identifies the part to be observed, the part not to be observed, or the like from the pixel values and determines the position at which a notification of the recognition result is to be presented. At this time, the notification position determination unit 116 may use the pixel values directly. Alternatively, as illustrated in FIG. 7 described below, the notification position determination unit 116 may divide an area surrounding the region of interest into a plurality of sub-areas and determine the notification position of the type information on the basis of the pixel values in the sub-areas. Additionally or alternatively, the mode or the like in the distribution of pixel values in the region of interest may be used. The notification position determination unit 116 may set a reference value for pixel values for identifying the part to be observed or the part not to be observed, in accordance with the user's operation. For example, the notification position determination unit 116 may set a reference value for the pixel values in accordance with the user's operation and determine the notification position of the type of the region of interest in a region having pixel values greater than or equal to the set reference value within an area surrounding the region of interest. The notification position determination unit 116 may determine the notification position of the type of the region of interest on the basis of pixel values in an area surrounding the region of interest and the type of the detected region of interest. For example, a reference range of pixel values may be set in advance for each type of region of interest, and the notification position of the type of the region of interest may be determined within a region having pixel values within the reference range within an area surrounding the region of interest. As a result, a notification can be presented at an appropriate notification position in accordance with the type of the region of interest. The notification position determination unit 116 may set a reference value for each color of pixels in advance and determine the notification position of the type of the region of interest on the basis of the reference value for a specific color.

FIG. 7 is a diagram illustrating still another example notification (example display) of the first notification information and the second notification information. In the example illustrated in FIG. 7, the notification position determination unit 116 divides the area of the rectangular shape 520 into six sub-areas in the horizontal direction and four sub-areas in the vertical direction in FIG. 7, and determines that the position of the type information is in a lower left sub-area whose average of the pixel values is high. As in the example in FIG. 6, the display control unit 112 superimposes the text 534 ("Pancreas") indicating the type information (second notification information) at an end of a leader line having another end located at the symbol 532. The notification information determination unit 114, the notification position determination unit 116, and the notification form determination unit 117 (processor) can set a division pattern of the rectangular shape 520 as illustrated in FIG. 7 in accordance with the user's operation via a setting screen as illustrated in FIG. 4.

Figure 8:
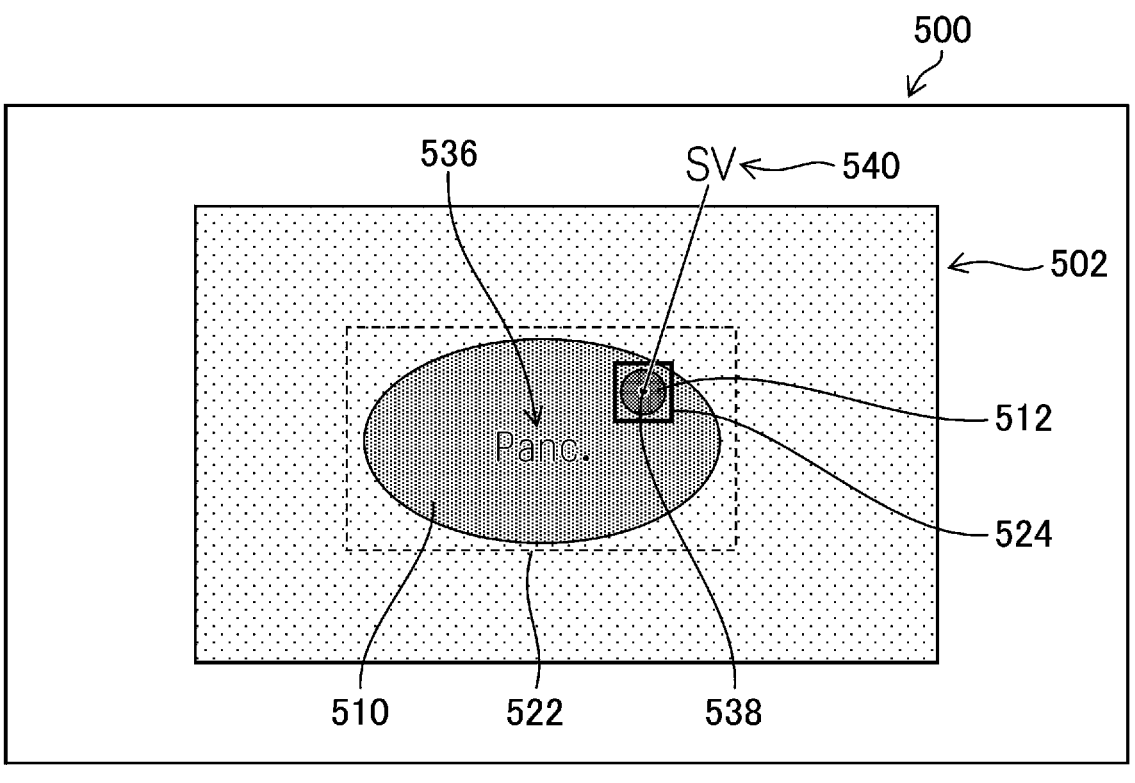
FIG. 8 is a diagram illustrating that a notification position of type information (second notification information) is determined in accordance with the type of a region of interest.

Determination, Display, and Recording of Notification Position based on Type of Region of Interest FIG. 8 is a diagram illustrating that the notification position of the type information (second notification information) is determined in accordance with the type of a region of interest. In the example in FIG. 8, the ultrasound image 502 shows the region of interest 510 (the pancreas) and a region of interest 512 (the splenic vein), and a notification of the region of interest 510 is provided using a rectangular shape 522 (bounding box or first notification information) indicating the position thereof and text 536 ("Panc.", which is an abbreviation for "Pancreas") indicating the type thereof. The text 536 is superimposed on the region of interest 510 at the center (center of gravity) thereof to provide a notification. In contrast, a notification of the region of interest 512 is provided using a rectangular shape 524 (bounding box or first notification information) indicating the position thereof and text 540 ("SV", which is an abbreviation for "splenic vein") indicating the type thereof. The text 540 is not superimposed on the region of interest 512, but is displayed at an end of a leader line having another end located at a symbol 538 superimposed on the region of interest 512 at the center (center of gravity) thereof. As a result, the text 540 does not hide the region of interest 512. Accordingly, the endoscope system 2 can present a notification of the type information (second notification information) at an appropriate notification position on the basis of the type of the region of interest.

As described above, the endoscope system 2 according to the first embodiment enables appropriate notification of a recognition result of a region of interest.

Applications to Other Medical Images

In the first embodiment described above, a description has been given of recognition and notification using an endoscopic ultrasound image, which is an aspect of a medical image. However, the image processing apparatus, the image processing system, the image processing method, and the image processing program according to the present invention can also be applied to a case where an ultrasound image acquired by an ultrasound apparatus (such as a body-surface endoscope apparatus) other than an endoscope, an endoscopic image acquired by an optical endoscope apparatus that captures an image of a subject by using normal light (white light) and/or special light (such as narrow-band light), or a medical image other than an endoscopic ultrasound image which is acquired by a CT apparatus, an MRI apparatus, a mammography apparatus, or the like, is used.

For example, when an endoscopic image acquired by an optical endoscope is used, the endoscope processor device 14 (image processing apparatus or processor) of the endoscope system 2 described above can perform processing similar to that of the ultrasonic processor device 12 according to the first embodiment. When an endoscopic image acquired by an optical endoscope is used, one or more of a plurality of image signals of red, green, blue, and the like can be used to determine notification information, a notification position, and a notification form and provide a notification. For example, a normal portion of the inner wall of the lumen may be reddish, and a lesion portion (region of interest) thereof may be blackish. In this case, the weight of the value (pixel value) of an image signal of a specific color can be increased (or decreased) to present a notification in the portion of the specific color or to present a notification in a portion other than the region of the specific color.

Application to Images other than Medical Images

The image processing apparatus, the image processing system, the image processing method, and the image processing program of the present invention can also be applied to images other than medical images. For example, the present invention can also be applied to an image acquired by an industrial endoscope that inspects damage, defects, and the like inside a tubular structure such as a pipe. The present invention can also be applied to inspection of damage, defects, and the like of a building such as a bridge, a road, or a tunnel from a captured image of the building. In these cases, the type of damage or defects can be considered to be "type information".

In the case of recognition and notification of the position and type of a photographic subject (such as a road, a person, a vehicle, or a building) in an image captured by an in-vehicle camera or a monitoring camera, the present invention can also be applied to, for example, superimposed display of type information (in this case, the photographic subject is a person) on the image in a location other than the face of a person.

While an embodiment and other examples of the present invention have been described, the present invention is not limited to the aspects described above, and various modifications may be made.

REFERENCE SIGNS LIST

2 endoscope system
10 ultrasound scope
12 ultrasonic processor device
14 endoscope processor device
16 light source device
18 monitor
20 insertion section
20a longitudinal axis
22 handheld operation section
24 universal cord
26 ultrasonic connector
28 endoscope connector
30 light source connector
32 tube
34 tube
36 air/water supply button
38 suction button
42 angle knob
44 treatment tool insertion port
50 tip main body
52 bending part
54 soft part
62 ultrasound probe
64 balloon
70 water supply tank
72 suction pump
100 transmitting/receiving unit
102 image generation unit
104 CPU
106 region-of-interest recognition unit
108 recording control unit
110 communication control unit
112 display control unit
114 notification information determination unit
116 notification position determination unit
117 notification form determination unit
118 memory
120 recording unit
500 screen
502 ultrasound image
510 region of interest
512 region of interest
520 rectangular shape
522 rectangular shape
524 rectangular shape
530 geometric shape
534 text
536 text
540 text
S100 to S180 step of image processing method

What is claimed is:

1. An image processing apparatus comprising a processor configured to execute:
an image acquisition process for acquiring an image;

a recognition process for recognizing a region of interest from the image and calculating probability information indicating a certainty of recognition of the region of interest;

a notification information determination process for determining first notification information indicating a position of the region of interest in the image and second notification information indicating a type of the region of interest; and a notification position determination process for determining a notification position at which a notification of the second notification information is to be presented in the image, on the basis of the probability information and pixel values in an area surrounding the region of interest in the image, wherein the notification position is within the region of interest, and wherein the second notification information is superimposed on the region of interest.

2. The image processing apparatus according to claim 1, wherein the processor is configured to, in the notification position determination process, determine the notification position further on the basis of the type of the region of interest.

3. The image processing apparatus according to claim 1, wherein the processor is configured to, in the notification position determination process, determine a center of gravity of the region of interest as the notification position.

4. The image processing apparatus according to claim 1, wherein the processor is configured to:

acquire time-series images in the image acquisition process; and in the notification position determination process, determine the notification position on the basis of a change over time in the probability information in the time-series images.

5. The image processing apparatus according to claim 4, wherein the processor is configured to:

in the notification position determination process, determine the notification position on the basis of a change over time in the pixel values in the time-series images.

6. The image processing apparatus according to claim 1, wherein the processor is configured to further execute a notification form determination process for determining a notification form of the second notification information.

7. The image processing apparatus according to claim 6, wherein the processor is configured to:

acquire time-series images in the image acquisition process; and in the notification form determination process, determine the notification form on the basis of a change over time in the pixel values in the time-series images.

8. The image processing apparatus according to claim 6, wherein the processor is configured to:

acquire time-series images in the image acquisition process;

in the notification position determination process, determine the notification position on the basis of a change over time in a size of the region of interest in the time-series images; and in the notification form determination process, determine the notification form on the basis of a change over time in the size of the region of interest in the time-series images.

9. The image processing apparatus according to claim 7, wherein the processor is configured to:

in the notification position determination process, determine the notification position on the basis of a change over time in a size of the region of interest in the time-series images; and in the notification form determination process, determine the notification form on the basis of a change over time in the size of the region of interest in the time-series images.

10. The image processing apparatus according to claim 1, wherein the processor is configured to superimpose the first notification information and the second notification information on the image and record the superimposed first notification information and second notification information in a recording device.

11. The image processing apparatus according to claim 1, wherein the processor is configured to record the second notification information and/or the notification position in a recording device.

12. The image processing apparatus according to claim 1, wherein the processor is configured to acquire a medical image of a subject in the image acquisition process.

13. An image processing system comprising:

the image processing apparatus according to claim 1; and an imaging device that captures the image.

14. The image processing system according to claim 13, wherein the imaging device is an endoscope.

15. The image processing system according to claim 14, wherein the endoscope is an ultrasonic endoscope.

16. The image processing system according to claim 13, wherein the processor is configured to cause a display device to display the image, the first notification information, and the second notification information in a superimposed manner.

17. The image processing system according to claim 16, further comprising the display device.

18. An image processing method executed by an image processing apparatus comprising a processor, the processor being configured to execute:

an image acquisition step of acquiring an image;

a recognition step of recognizing a region of interest from the image and calculating probability information indicating a certainty of recognition of the region of interest;

a notification information determination step of determining first notification information indicating a position of the region of interest in the image and second notification information indicating a type of the region of interest; and a notification position determination step of determining a notification position at which a notification of the second notification information is to be presented in the image, on the basis of the probability information and pixel values in an area surrounding the region of interest in the image, wherein the notification position is within the region of interest, and wherein the second notification information is superimposed on the region of interest.

19. A non-transitory, computer-readable tangible recording medium storing a program for causing, when read by a computer, the computer to execute the image processing method according to claim 18.

* * * * *